United States Patent [19]
Griffis et al.

[11] Patent Number: 5,282,940
[45] Date of Patent: Feb. 1, 1994

[54] METHOD FOR REDUCING OR ELIMINATING MICROORGANISMS IN SUBSTANCES BY ELECTRIC STIMULATION

[75] Inventors: Carl L. Griffis, Fayetteville; Michael F. Slavik, Springdale; Phillip V. Engler; Yanbin Li, both of Fayetteville, all of Ark.

[73] Assignee: The Board of Trustees of the University of Arkansas, Little Rock, Ark.

[21] Appl. No.: 917,796

[22] Filed: Jul. 20, 1992

Related U.S. Application Data

[63] Continuation of Ser. No. 553,984, Jul. 17, 1990, abandoned.

[51] Int. Cl.$^5$ ............................................. C02F 1/00
[52] U.S. Cl. ................................. 204/131; 204/149; 426/237; 426/244
[58] Field of Search ............... 204/131, 149; 426/237, 426/244

[56] References Cited

U.S. PATENT DOCUMENTS

| | | | |
|---|---|---|---|
| 3,058,894 | 10/1962 | Hallum | 204/131 |
| 3,625,843 | 12/1971 | Doevenspeck | 426/241 |
| 3,753,886 | 8/1973 | Myers | 204/149 |
| 3,841,483 | 10/1974 | Overton | 210/87 |
| 3,936,364 | 2/1976 | Middle | 426/66 |
| 4,457,221 | 7/1984 | Geren | 426/244 |
| 4,761,208 | 8/1988 | Gram et al. | 204/95 |
| 4,838,154 | 6/1989 | Dunn et al. | 99/451 |

OTHER PUBLICATIONS

Dickson et al., "Effect of Electrical Charge on Attachment of Salmonella typhimurium to Meat Surfaces," J. Food Science, vol. 54, No. 3. 516-520 (1989), TX 341 F8.
Elsevier Biomedical Press (1982) pp. 227-277-U. Zimmermann "Electric Field-Mediated Fusion and Related Electrical . . . ".
Advances in Meat Research-vol. 1, Electrical Stimulation, A. M. Pearson & T. R. Dutson AVI Publishing Co., Inc. pp. 237-276.
CRC Critical Reviews in Food Science and Nutrition, vol. 18, Issue 1, pp. 1-58 "Post-Mortem Stimulation of Carcasses . . . ".
Journal of Food Protection, vol. 3 Sep. 1980, "Bacteriology of Electrically Stimulated Carcasses" pp. 686-705.
Biochimica et Biophysica Acta pp. 789-800, No. 148 (1967) "Effects of High Electric Fields on Microorganisms" No. II.
Biochimica et Biophysica Acta pp. 781-788, No. 148 (1967) "Effects of High Electric Fields on Microorganisms" No. I.
Biochimica et Biophysica Acta. 763 (1983), pp. 325-331, "Effects of Pulsed Electric Fields on Mouse . . . " G. K. Smith et al.
Journal of Food Protection, vol. 44, Jul. 1961, pp. 545-549, 564. "Microbiology of Hot-Boned and Electrostimulated Meat".

Primary Examiner—John Niebling
Assistant Examiner—Arun S. Phasge
Attorney, Agent, or Firm—Hermann Ivester, Hill, Steadman and Simpson

[57] ABSTRACT

A method for the reduction or elimination of microbes in liquid or food products whereby the passage of a waveform, such as a DC square-wave, of a specific amplitude, duty cycle and current through the liquid or food product for a specific time period, allows for the elimination of microbes such as Salmonella Typhimurium from a variety of substances, including water, milk and solid food products.

4 Claims, 1 Drawing Sheet

METHOD FOR REDUCING OR ELIMINATING MICROORGANISMS IN SUBSTANCES BY ELECTRIC STIMULATION

This invention was made with Government support under Grant No. 890234 awarded by the Department Of Agriculture.

This is a continuation of application Ser. No. 553,984 filed Jul. 17, 1990 now abandoned.

BACKGROUND OF THE INVENTION

1. Field of the Invention

The invention relates to a method for electrically stimulating substances, such as liquids or food products, to reduce or eliminate live microorganisms present therein.

2. Description of the Prior Art

Known methods for reducing live microorganisms in substances include the application of heat, chemicals, and irradiation. All of these methods are expensive. Further, the application of chemical treatments to food products is unacceptable, as it requires the addition of dangerous chemicals to either the processing water or the liquids undergoing treatment.

SUMMARY OF THE INVENTION

The present invention provides a method for the reduction or elimination of live microorganisms in a substance by electric stimulation. A direct current pulse square-wave is passed through a substance, such as water, milk, or solid food products, for a specified time period, resulting in the reduction or elimination of live microorganisms, such as Salmonella typhimurimum.

Microbial contamination of food products, including cross-contamination of food during processing in water, can be reduced or eliminated with the use of this invention and should benefit the dairy, poultry, beef, pork and fish industries, as well as other food processing operations that use water or other liquids during processing.

DESCRIPTION OF THE PREFERRED EMBODIMENTS

Figure 1:
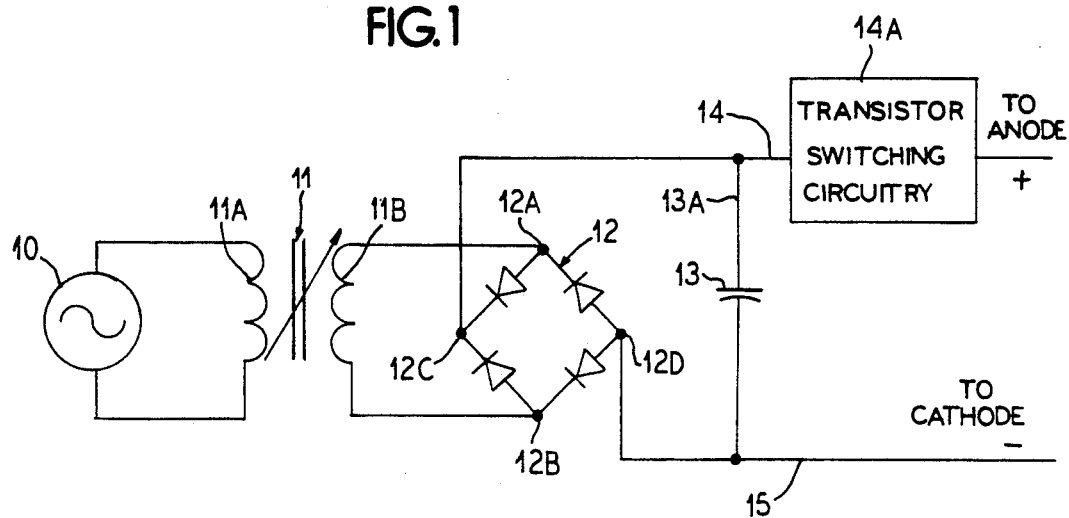
FIG. 1 shows a schematic plan view of a direct current power supply for generating variable voltages in accordance with the principles of the present invention.
Figure 2:
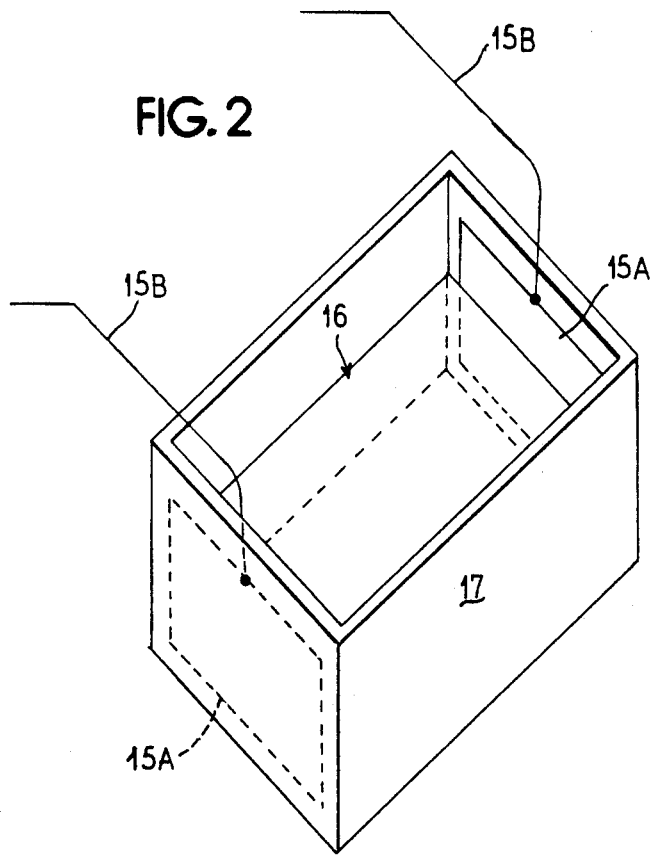
FIG. 2 is a isometric view of a polycarbonate tub containing platinum electrodes, where the platinum electrodes may be selectively connected to the power supply of FIG. 1 for the purposes of the present invention.

In FIG. 1, a variable transformer 11 is supplied an input signal of 120 v ac by the input 10 at the primary winding 11A. In order to provide a direct current square-wave pulse, the secondary winding 11B is electrically connected to a bridge rectifier 12 at 12A and 12B. The bridge rectifier 12 is in turn electrically connected via a positive voltage terminal 12C to a circuit 14, having a transistor switching means 14A. The negative voltage terminal 12D may be selectively connected to a circuit 15 having a plurality of electrodes 15A (FIG. 2). A filter capacitor 13 is connected across circuits 14 and 15 via the circuit line 13A.

The exemplary disclosure of FIG. 1 contemplates provision of a direct current square-wave pulse. However, it is contemplated by the present invention that the signal generating means of the present invention can also comprise means for producing a ramping pulse, a sine wave pulse, and/or a sawtooth pulse, such as by modifying the transistor switching means 14A, as known to those of ordinary skill in the art.

As shown in FIG. 2, a polycarbonate tub 17 contains a plurality of electrodes 15A, which may be selectively connected to the positive and negative poles of the power supply (FIG. 1) by a plurality of leads 15B. Also shown is a supply of liquid 16, which is either liquid under treatment, or is a body of liquid providing an electrolytic bath to insure electrical conductively in which substances, such as relatively solid food products, may be immersed in accordance with this invention. It is further contemplated that the killing of microbes in the electrolytic bath prevents the cross-contamination of subsequent food substances immersed therein.

In accordance with this invention, a substance, such as a food product, may be placed within the polycarbonate tub 17. The plurality of electrodes 15A are then lowered into the polycarbonate tub 17 and are connected to selected terminals of the power supply of FIG. 1. If necessary to insure conductivity, an electrolytic solution is added in sufficient quantities to allow the passage of an electric current through the supply of liquid 16. A selected square-wave pulse is generated, and is directed into the body of the liquid 16 via the plurality of electrodes 15. The square-wave pulse is passed through the liquid 16 for a time period sufficient length to kill the microorganisms which may be present.

Described below are two examples of the method of eliminating live microorganisms by electric stimulation within specified substances.

EXAMPLE 1

Five liters of a sodium chloride solution in water were placed in a polycarbonate tub 17. The solution contained 0.85% sodium chloride by weight. A portion of a culture containing approximately one billion Salmonella Typhimurium per milliliter was added to the sodium chloride, such that the final solution contained two hundred thousand microbes per milliliter. The two platinum electrodes 15A were lowered into the solution, such that the electrodes 15A were positioned at opposing sides of the polycarbonate tub 17. One of the electrodes 15A was attached to a positive pole of the power supply (FIG. 1), and the other electrodes 15A was attached to the negative pole of the power supply (FIG. 1). The power supply of FIG. 1 was used to generate a square-wave pulse between the electrodes 15A. A current of 0.5 amps is delivered to the solution, at a frequency of 0.67 Hz and a duty cycle of 67%, by a 15 volt square-wave pulse. After the voltage and current were applied for thirty minutes, analysis of the solution showed that no Salmonella were left alive. While the techniques exemplified by the foregoing example illustrate the applicability of the invention to milk and other liquids, the same methodology and the same general type of apparatus can be used in connection with solid foods such as meat and other products. For example, in the industrial processing of poultry, liquid immersion of carcasses is contemplated.

EXAMPLE 2

Using an apparatus similar to that of FIGS. 1 and 2, five liters of an electrolytic sodium chloride solution containing 0.85% sodium chloride by weight were placed in a polycarbonate tub 17. A culture containing approximately one billion Salmonella per milliliter was added to the supply of liquid such that approximately two hundred thousand microorganisms per milliliter existed in the final solution. Five chicken drumsticks were dipped into a Salmonella culture, containing one hundred million microbes per milliliter, for thirty minutes. Such a step was merely to insure that each drumstick was inoculated with the offending microbes, thereby establishing the validity of the invention. The positive pole of the power supply (FIG. 1) was attached to each of the bony ends of the drumsticks. The drumsticks were then lowered into the electrolytic solution until they were fully immersed.

A direct current square-wave pulse was generated and supplied between the electrode 15A and the drumsticks, where the duty cycle was 67%, the frequency was 0.67 Hz, and the amplitude of the square-wave was 30 volts, which resulted in a current of 0.1 amps per drumstick.

After the voltage and current had been applied for thirty minutes, analysis of the solution and the drumsticks showed there were no living Salmonella in the solution, and that the number of living Salmonella on the drumsticks had been significantly reduced.

We have used other frequencies, duty cycles, voltage and currents to successfully eliminate microbes in solution and to reduce the number on pieces of meat such as chicken drumsticks. We have also successfully killed microbes other than *Salmonella Typhimurimum*.

We have found it satisfactory to have a current in range of 0.1 to 1.5 amps, a frequency in a range from 0.3 to 100,000 Hz, a duty cycle in a range of 1 to 67%, and a voltage in the range from 12 to 100 volts.

Although other modifications and changes may be suggested by those skilled in that art, it is the intention of the inventor to embody with the patent warranted hereon all changes and modifications as reasonably and properly come within the scope of his contribution to the art.

I claim:

1. A method for eliminating a number of live microorganisms in a batch of liquid by electric simulation, including the steps of:
   a) establishing a static treatment zone within the confines of a tub, and charging a predetermined batch of liquid into the treatment zone by replacing said batch of liquid within the tub;
   b) rendering said batch of liquid electrically conductive by adding an electrolytic solution to said batch of liquid within said tub in sufficient supply to render said batch of liquid electrically conductive;
   c) generating and applying, via a platinum electrode, a dc signal having no polarity reversal in the form of a 30 volt square wave pulse to said batch of liquid;
   d) continuing the passage of said dc signal through said batch of liquid for a predetermined time period to kill said number of live microorganisms; and
   e) immersing a food substance containing Salmonella Typhimurium in said batch of liquid and retaining said food substance in said batch of liquid during step (d) to electrically kill live microorganisms in said food substance.

2. A method for eliminating a number of live microorganisms in a food substance by the passage of an electric current therethrough, including the steps of:
   a) establishing a static treatment zone within the confines of a tube, and charging a predetermined batch of liquid into the treatment zone by placing said batch of liquid within the tub;
   b) rendering said batch of liquid electrically conductive by adding an electrolytic solution to said batch of liquid within said tub in sufficient supply to render said batch of liquid electrically conductive;
   c) adding said food substance to said batch of liquid;
   d) generating and supplying, via a platinum electrode, a dc signal having no polarity reversal to said batch of liquid; and
   e) continuing the passage of said dc signal through said batch of light for a sufficient time period to electrically kill said number of live microorganisms in said food substance, without increasing the temperature of said batch of liquid more than 5° C. within said tub, wherein said food substance is chicken.

3. A method for preventing or reducing microbial cross contamination between a plurality of food substances, including the steps of:
   a) establishing a static treatment zone within the confines of a tub, and charging a predetermined batch of liquid into the treatment zone by placing said batch of liquid within the tub;
   b) adding a first food substance to said batch of liquid;
   c) rendering said batch of liquid electrically conductive by adding an electrolytic solution to said batch of liquid within said tub in sufficient supply to render said batch of liquid electrically conductive;
   d) generating and supplying, via a platinum electrode, a dc signal having no polarity reversal to said batch of liquid by providing an ac input passing said ac input through a variable transformer to produce an electric signal, passing said electric signal through a bridge rectifier to produce a full wave rectified signal, and passing said full wave rectified signal through a circuit to produce said dc signal, and then applying said dc signal to said batch of liquid;
   e) continuing the passage of said dc signal through said batch of liquid for a predetermined time period to electrically kill a number of live microorganisms present therein, without increasing the temperature of said batch of liquid more than 5° C. within said tub;
   f) removing said first food substance;
   g) adding a subsequent food substance; and
   h) repeating steps (c), (d) and (e).

4. A method as defined in claim 3, further comprising repeating steps (g) and (h) substantially free of cross contamination.

* * * * *